United States Patent [19]

Harada et al.

[11] Patent Number: 5,362,897
[45] Date of Patent: Nov. 8, 1994

[54] PROCESS FOR PRODUCING TRIALKOXYSILANES

[75] Inventors: Katsuyoshi Harada, Oka; Yoshinori Yamada, Aichi, both of Japan

[73] Assignee: Toagosei Chemical Industry Co., Ltd., Tokyo, Japan

[21] Appl. No.: 229,921

[22] Filed: Apr. 19, 1994

[30] Foreign Application Priority Data

| Apr. 30, 1993 | [JP] | Japan | 5-124737 |
| May 11, 1993 | [JP] | Japan | 5-132962 |
| May 11, 1993 | [JP] | Japan | 5-132963 |

[51] Int. Cl.$^5$ ............................. C07F 7/04; C07F 7/18
[52] U.S. Cl. ................................................... 556/470
[58] Field of Search ........................................ 556/470

[56] References Cited

U.S. PATENT DOCUMENTS

| 4,762,939 | 8/1988 | Mendicino | 556/470 |
| 4,778,910 | 10/1988 | Stoffer et al. | 556/470 |
| 4,999,446 | 3/1991 | Moody et al. | 556/470 |
| 5,084,590 | 1/1992 | Ritscher et al. | 556/470 |
| 5,260,471 | 11/1993 | Yamada et al. | 556/470 |

*Primary Examiner*—Paul F. Shaver
*Attorney, Agent, or Firm*—Henry T. Burke

[57] ABSTRACT

In a process for producing trialkoxysilanes by reaction of a metallic silicon and an alcohol having 1 to 4 carbon atoms, the reaction is effected (1) using as the metallic silicon one containing 0.30 to 0.37% by weight of aluminum, (2) using as the catalyst cuprous chloride prepared by a wet process, and (3) allowing aluminum and/or an aluminum compound to coexist, thereby securing a high conversion rate of metallic silicon, and accordingly decreasing the amount of unreacted metallic silicon and suppressing discharge of industrial wastes with eliminating environmental problems.

12 Claims, No Drawings

PROCESS FOR PRODUCING TRIALKOXYSILANES

This invention relates to a process for efficiently producing trialkoxysilanes, which are useful as materials for silane-coupling agents and others.

Alkoxysilanes are useful as materials for various silane-coupling agents and for insulating films. Particularly, trialkoxysilanes, which have an Si-H linkage in the molecule and are chemically stable as compared with monoalkoxysilanes and dialkoxysilanes, have been highly demanded, and their low-cost, efficient manufacturing method has been sought.

Hitherto, a process using chlorosilanes and lower alkyl alcohols as materials has been known as the manufacturing method for trialkoxysilanes. However, it has some disadvantages due to high cost of chlorosilanes, difficulty in purification of the product owing to by-production of hydrochloric acid besides objective alkoxysilanes, and corrosion of the reaction apparatus.

On the other side, a process, called "direct method", by the reaction of metallic silicon and an alkyl alcohol has been known. The process is carried out in gas or liquid phase in the presence of a copper catalyst, for example. This may be advantageous from the industrial and economical viewpoints, since trialkoxysilanes are obtained by one step reaction. However, it has yet a big problem in its low silicon conversion rate, and also provides another environmental problem because it discharges much amount of unreacted metallic silicon as industrial wastes.

In view of such problems as mentioned above, the present inventors have made an intensive research for a process of producing trialkoxysilanes, which gives a high conversion rate of metallic silicon, a decreased amount of unreacted metallic silicon, and a suppressed amount of industrial wastes with eliminating environmental problems, and then has accomplished the present invention.

The present invention relates to a process for producing trialkoxysilanes by reaction of a metallic silicon and an alcohol having 1 to 4 carbon atoms, in which the reaction is effected under at least one of the following conditions (1)-(3):

(1) using as the metallic silicon one which contains 30 to 0.37% by weight of aluminum,
(2) in the presence of a catalyst of cuprous chloride prepared by a wet process, and
(3) allowing aluminum and/or an aluminum compound to coexist.

Metallic silicon used as one of the materials in the present invention is suitably one having a purity of 80% by weight or more. Metallic silicon may contain up to about 1% by weight each of Al, Fe, Ca, and other impurities. A metallic silicon washed with fluoric acid or the like may also be used.

Metallic silicon more suitably used in the present invention is one containing 0.30 to 0.37%, preferably 0.31 to 0.36%, particularly 0.32 to 0.35%, by weight of aluminum. Conversion rate of metallic silicon is particularly improved when metallic silicon containing such an amount of aluminum is used. Aluminum contained in the metallic silicon may possibly be present in the form of metallic aluminum, an aluminum compound, an aluminum alloy or the like, and the aluminum content referred to in the present invention means a value calculated as aluminum atoms.

To produce metallic silicon having a controlled amount of aluminum, a method in which, for example, ferrosilicon preferably containing about 92% by weight of silicon, is made react with an iron chloride solution in hydrochloric acid, is suitable.

Metallic silicon used in the present invention is suitably granular. There is little limitation in granular size, but a granular diameter on average is preferably 2 mm or less, more preferably 25 to 500 $\mu$m, most preferably 50 to 300 $\mu$m.

Lower alkyl alcohols having 1 to 4 carbon atoms, which are another raw material, may be either straight chain or branched chain, specifically, methanol, ethanol, n-propanol, isopropanol, n-butanol, sec-butanol, isobutanol, tert-butanol, among which methanol and ethanol are preferred, and ethanol is the most preferred.

The lower alkyl alcohols are preferably of a purity of 95% by weight or more, and are more preferably those treated with a dehydrating agent to have a water content of not more than 2,000 ppm, preferably not more than 500 ppm.

Feeding rate of the lower alkyl alcohol to the reaction system is preferably 10 to 1,000 millimols/hour, more preferably 50 to 500 millimols/hour, per 1 mole of metallic silicon. Within such ranges, economically good results are secured with a high conversion rate of metallic silicon and a small amount of unreacted lower alkyl alcohol.

The lower alkyl alcohol may be supplied as it is, or after diluted with a dilution gas. The dilution gas is not specifically limited so far as it does not react with the materials and trialkoxysilanes. Nitrogen, argon, hydrogen, or the like may be exemplified.

Catalysts used in the invention are not specifically restricted and may be those conventionally used, such as copper catalysts, zinc catalysts, nickel catalysts and the like, among which copper catalysts are preferred. Specifically, copper salts, such as cuprous chloride, cupric chloride, copper bromide, copper iodide, copper fluoride, copper carbonate, copper sulfate, copper acetate, copper oxalate, copper thiocyanate and the like; copper-containing inorganic compounds, such as cuprous hydroxide, cuptic hydroxide, copper cyanide, copper sulfide, copper oxide and the like; organic copper compound, such as methylcopper, ethylcopper, and the like; and metallic copper, may be illustrated. Among them, cuprous chloride is more preferable, and, particularly, cuprous chloride prepared by a wet process is preferred. Hereinafter, the invention will be explained with respect to such cuprous chloride.

Cuprous chloride prepared by a wet process (hereinafter referred to as "wet process cuprous chloride") means one prepared through steps of crystallization and separation from a solution and drying. Specifically, a preparing method in which copper flakes are added to an aqueous cupric chloride solution and the resulting cuprous chloride crystals are separated and dried; or a preparing method in which copper sulfate, hydrochloric acid, copper and sodium chloride are subjected to a solution reaction, and the crystals of the resulting cuprous chloride are separated and dried, is illustrated.

Wet process cuprous chloride is clearly distinct from cuprous chloride prepared by a dry process, namely that prepared using metallic copper and chlorine gas as the materials.

As for the wet process cuprous chloride, one having a purity not less than 90% by weight is preferred, by which metallic silicon conversion rate can be increased.

Granular diameter of the wet process cuprous chloride is preferably less than 40 μm, more preferably less than 2 μm. Use of wet process cuprous chloride of such a granular diameter much more increases the reaction rate and increases the conversion rate of metallic silicon.

The granular size of wet process cuprous chloride can be controlled by modifying the preparation conditions. If it is too fine, efficiencies in crystallization and drying steps in the preparing process are lowered, and the surface of the granules tends to be deactivated by heat, moisture, etc. As a particularly suitable process, therefore, a method is illustrated in which wet process cuprous chloride is so prepared as to be of a granular diameter not less than 20 μm, and then the granules are pulverized to a diameter of less than 2 μm by means of ball mill or the like. The pulverization is preferably conducted in air with least moisture, more preferably in nitrogen.

The catalyst may be fed to the reaction system, separately from metallic silicon, or in the form of a mixture with metallic silicon or in the form carried on metallic silicon, preferably after the catalyst has been activated. For activation, a heat-treatment at a temperature of 100° C. to 600° C., more preferably 130° C. to 230° C., is preferred. At a temperature lower than 100° C., it is not efficient since it needs a longer activation period of time, and, at a temperature higher than 600° C., it might cause deactivation of the catalyst. In case of liquid phase reaction, the catalyst may be activated before added to a solvent or in a solvent while an inert gas is blown into it.

Amount of the catalyst used is preferably 0.5 to 50 parts, more preferably 5 to 30 parts, by weight based on 100 parts by weight of metallic silicon. Amounts less than 0.5 part and more than 50 parts by weight tend to cause a decrease in conversion rate of silicon.

For the purpose of further increasing the silicon conversion rate, in the present invention, it is desirable to allow aluminum and/or an aluminum compound (hereinafter generally called as "aluminums") to coexist in the reaction system. The aluminums referred to herein should be understood to be distinct from aluminum contained in metallic silicon.

As the aluminums, aluminum metals, such as metallic aluminum, aluminum alloys with Si, Mg and Ca; aluminum halides, such as aluminum chloride, aluminum bromide, aluminum fluoride, aluminum iodide and the like; aluminum salts, such as aluminum carbonate, aluminum sulfate and the like; other aluminumcontaining inorganic compounds, such as aluminum hydroxide, aluminum sulfide and the like; and aluminum-containing organic compounds, such as aluminum acetate, aluminum oxalate, trialkoxyaluminums and the like, may be illustrated, among which aluminum metals, such as metallic aluminum and aluminum alloys, are preferred. The aluminums may be used singly or in a combination of two or more kinds.

The aluminums are preferably used in an amount of 0.01 to 10 parts, more preferably 0.1 to 2 parts, by weight based on 100 parts by weight of metallic silicon. Within such ranges, significant increase in silicon conversion rate is secured.

In case of using aluminum alloys as the aluminums, those containing not less than 50% by weight of aluminum are preferred. Those containing not less than 85% by weight are more preferred.

The aluminums may be fed to the reaction system, singly or as a mixture with metallic silicon or the catalyst.

The reaction of the present invention can be conducted in gas or liquid phase, but a liquid phase reaction is much preferred. Hereinafter, the invention will be further explained with respect to the liquid phase reaction as examples.

There is no limitation for the shape of a reactor, so far as metallic silicon is kept in a well-dispersed state in the reactor. It may have an outside jacket for cooling or heating, or inside fins or coils for improving heat transmission.

The reactor is suitably equipped with a tube for feeding the reactants, namely material silicon and alcohols; a tube for discharging a liquid reaction product containing trialkoxysilane as a main component and other silicon compounds and unreacted alcohols as by-products; and an outlet for discharging the residue after reaction.

Material for the reactor may be chosen within the broad range of kinds, such as quartz, glass, metals and the like.

System of the reaction may be either in batch wherein the whole amounts of metallic silicon and the catalyst are initially fed, or continuous wherein metallic silicon and the catalyst are continuously fed during the course of reaction.

In case of liquid phase reaction, a solvent is used. There is no specific limitation for the solvent, so far as it is inert to metallic silicon, the catalyst and trialkoxysilanes. However, stable solvents having a relatively high boiling temperature are preferred. For example, paraffinic hydrocarbons, such as octane, decane, dodecane, tetradecane, hexadecane, octadecane, eicosane and the like; alkylbenzene hydrocarbons, such as diethylbenzene, trimethylbenzene, cymene, butylbenzene, butyltoluene, octylbenzene, dodecylbenzene and the like, and hydrogenated products thereof; diphenyl hydrocarbons, such as diphenyl, diphenyl ether, monoethyldiphenyl, diethyldiphenyl, triethyldiphenyl and the like, and hydrogenated products thereof; alkylnaphthalene hydrocarbons and hydrogenated products thereof; and triphenyl hydrocarbons and hydrogenated products thereof, are illustrated, among which alkylbenzene hydocarbons are preferred, and dodecylbenzene hydrocarbons are more preferred. These may be used singly or in a combination of two or more kinds.

Suitable ratio of metallic silicon to solvent is preferably 0.1 kg to 1 kg, more preferably 0.3 kg to 0.7 kg of metallic silicon to one liter of solvent.

The reaction temperature is preferably 100° C. to 300° C., more preferably 150° C. to 230° C. At a temperature lower than 100° C., the conversion rate of metallic silicon is not increased. At a temperature higher than 300° C., the lower alkyl alcohol is decomposed by contact with metallic silicon or the catalyst, and the generated moisture tends to deactivate the catalyst.

The reaction may be conducted under an atmospheric, pressurized or depressurized condition, but the reaction under atmospheric pressure is preferred because of its economical advantages rendered from the simple apparatus.

Trialkoxysilanes obtained by the present invention have the alkoxyl groups corresponding to lower alkyl alcohols that have been used as a material. Specifically, trimethoxysilane, triethoxysilane, tri-n-propoxysilane, triisopropoxysilane, tri-n-butoxysilane, tri-sec-butoxysilane, triisobutoxysilane, tri-tert-butoxysilane, and the like, are illustrated. As trioxysilanes produced according to the present invention, preferred are trimethoxysilane and triethoxysilane, and the most preferred is triethoxysilane.

The liquid reaction product contains a trialkoxysilane in a high concentration, besides a tetraalkoxysilane and other by-products, as well as an unreacted alcohol. The objective trialkoxysilane can be readily isolated from the liquid product according to a conventional procedure, such as distillation.

The reaction solvent that has been separated from the trialkoxysilane stays as a reddish brown slurry containing copper powder formed during the reaction, and unreacted metallic silicon. According to the process of the invention, amount of the reaction residue is small, because there remains little unreacted metallic silicon, so that the residue can be readily separated by filtration, centrifugation or similar means. The separated solid reaction residue is almost composed of copper powder, with little unreacted metallic silicon. The solvent recovered by filtration may be recycled.

The present invention will more fully be explained with respect to the following working and comparative examples, which are, however, only illustrative and never construed to be limitative.

In this specification, values in selectivity of trialkoxysilanes and in conversion rate of metallic silicon are those calculated according to the following equations:

Trialkoxysilane selectivity (mol %) =

[(trialkoxysilane mol)/ (trialkoxysilane mole + tetraalkoxysilane mol)] × 100

Metallic silicon conversion rate (wt %) =

100 − [(metallic silicon weight in the residue)/

(metallic silicon weight fed)] × 100

EXAMPLE 1

Into a 500 ml glass reactor equipped with a tube for feeding materials, a thermometer, a stirrer, a cooler and an outlet of coolant, was fed 300 ml of dodecylbenzene as solvent. Then, 150 g of metallic silicon (containing 99.1% by weight of silicon, 0.29% by weight of aluminum and 0.2% by weight of iron, with a granular diameter on average of 100 μm) and wet process cuprous chloride (95% purity) were fed thereto. While nitrogen (30 ml/min) was fed, the mixture was stirred and heated at 200° C. for 10 hours for catalyst activation treatment. The above wet process cuprous chloride had been prepared by subjecting copper sulfate, hydrochloric acid, copper and sodium chloride to a solution reaction, separating the thus-crystallized cuprous chloride, and drying it to obtain solid cuprous chloride, which was then pulverized by ball mill to a granular diameter of 0.06 to 1.48 μm.

While the reactor was kept at 180° C. under stirring with nitrogen (30 ml/min) being supplied, vaporized ethanol was fed through the feeding tube into the solvent at a rate of 50 g/hour for reaction.

Five minutes after commencement of the reaction, a liquid product began distilling out of the cooler. The composition of the distilled liquid product was occasionally analyzed by gas chromatography, and change in the composition with elapse of time was observed. The reaction was considered to finish when the ethanol content reached 100%.

The reaction finished after 23 hours from the commencement, and a liquid product containing objective triethoxysilane was obtained. Analytical results of the composition of the whole liquid product, as well as the corresponding selectivity of triethoxysilane and conversion rate of silicon, are shown in Table 1.

The content remaining in the reactor after separation of the trialkoxysilane was a reddish brown slurry. The solid reaction residue separated by filtration was almost copper powder with little amount of unreacted silicon. The solvent recovered by filtration was colorless and clear, which was able to be reused.

EXAMPLE 2

The reaction was repeated in the same manner as in Example 1, except that wet process cuprous chloride (prepared as in Example 1, but the ball mill treatment was omitted; 0.12 to 28 μm granular diameter) was used. The reaction finished after 22 hours.

Analytical results of the composition of the whole liquid product, as well as the corresponding selectivity of triethoxysilane and conversion rate of silicon, are shown in Table 1.

COMPARATIVE EXAMPLE 1

The reaction was repeated in the same manner as in Example 1, except that cuprous chloride prepared by a dry process from metallic copper and chlorine gas (subjected to ball milling; 0.04–1.63 μm granular diameter) was used. The reaction finished after 23 hours.

Analytical results of the composition of the whole liquid product, as well as the corresponding selectivity of triethoxysilane and conversion rate of metallic silicon, are shown in Table 1.

COMPARATIVE EXAMPLE 2

The reaction was repeated in the same manner as in Example 1, except that dry process cuprous chloride (prepared as in Comparative Example 1, but the ball mill treatment was omitted; 0.10 to 24 μm granular diameter) was used. The reaction finished after 21 hours.

Analytical results of the composition of the whole liquid product, as well as the corresponding selectivity of triethoxysilane and conversion rate of metallic silicon, are shown in Table 1.

TABLE 1

| | Catalysts | | | Time until finish of the reaction (hr) | Composition of product (wt %) | | | Selectivity of tri-compound (mol %) | Conversion rate of metallic Si (wt %) |
| --- | --- | --- | --- | --- | --- | --- | --- | --- | --- |
| | Preparation process | Ball mill treatment | Granular size (μm) | | Tri-compound*1 | Tetra-compound*2 | Unreacted alcohol | | |
| Example 1 | wet | yes | 0.06–1.48 | 23 | 54.2 | 6.7 | 39.1 | 91 | 87.5 |
| Example 2 | wet | no | 0.12–28 | 22 | 56.5 | 5.3 | 38.3 | 83 | 81.8 |
| Comparative Example 1 | dry | yes | 0.04–1.63 | 23 | 46.1 | 9.7 | 44.2 | 86 | 76.3 |

TABLE 1-continued

| | Catalysts | | | Time until finish of the reaction (hr) | Composition of product (wt %) | | | Selectivity of tri-compound (mol %) | Conversion rate of metallic Si (wt %) |
|---|---|---|---|---|---|---|---|---|---|
| | Preparation process | Ball mill treatment | Granular size (μm) | | Tri-compound*1 | Tetra-compound*2 | Unreacted alcohol | | |
| Comparative Example 2 | dry | no | 0.10–24 | 21 | 44.9 | 3.7 | 51.4 | 94 | 61.8 |

*1Tri-compound: triethoxysilane
*2Tetra-compound: tetraethoxysilane

EXAMPLE 3

The reaction was repeated in the same manner as in Example 1, except that metallic silicon containing 98.9% by weight of silicon, 0.38% by weight of aluminum and 0.43% by weight of iron and having a granular diameter on average of 100 μm was used, and, further, 1 g of powdered aluminum was allowed to coexist. The reaction finished after 23 hours.

Analytical results of the composition of the whole liquid product, as well as the corresponding selectiveity of triethoxysilane and conversion rate of metallic silicon, are shown in Table 2.

The content remaining in the reactor after separation of the trialkoxysilane was a reddish brown slurry. The solid reaction residue separated by filtration was almost copper powder with little amount of unreacted silicon. The solvent recovered by filtration was colorless and clear, which was able to be reused.

EXAMPLE 4

The reaction was repeated in the same manner as in Example 3, except that 1 g of aluminum silicon (containing 10% by weight of silicon) was used in place of the powdered aluminum. The reaction finished after 31 hours.

Analytical results of the composition of the whole liquid product, as well as the corresponding selectivity of triethoxysilane and conversion rate of silicon, are shown in Table 2.

EXAMPLE 5

The reaction was repeated in the same manner as in Example 4, except that the amount of aluminum silicon used was 0.5 g. The reaction finished after 23 hours.

Analytical results of the composition of the whole liquid product, as well as the corresponding selectivity of triethoxysilane and conversion rate of silicon, are shown in Table 2.

EXAMPLE 6

The reaction was repeated in the same manner as in Example 1, except that metallic silicon (containing 99% by weight of silicon, 0.32% by weight of aluminum and 0.37% by weight of iron, with a granular diameter on average of 100 μm) prepared by a reaction of ferrosilicon containing 92% by weight of silicon and an iron chloride solution in hydrochloric acid was used. The reaction finished after 26 hours.

Analytical results of the composition of the whole liquid product, as well as the corresponding selectivity of triethoxysilane and conversion rate of silicon, are shown in Table 3.

The content remaining in the reactor after separation of the triethoxysilane was a reddish brown slurry. The solid reaction residue separated by filtration was almost copper powder with little amount of unreacted silicon. The solvent recovered by filtration was colorless and clear, which was able to be reused.

EXAMPLE 7

The reaction was repeated in the same manner as in Example 6, except that metallic silicon (containing 99.0% by weight of silicon, 0.31% by weight of aluminum and 0.30% by weight of iron, with a granular diameter on average of 100 μm) was used. The reaction finished after 30 hours.

Analytical results of the composition of the whole liquid product, as well as the corresponding selectivity of triethoxysilane and conversion rate of silicon, are shown in Table 3.

EXAMPLE 8

The reaction was repeated in the same manner as in Example 6, except that metallic silicon (containing 99.0% by weight of silicon, 0.36% by weight of aluminum and 0.39% by weight of iron, with a granular diameter on average of 100 μm) was used. The reaction finished after 27 hours.

TABLE 2

| | Aluminum | | Time until finish of the reaction (hr) | Composition of product (wt %) | | | | Selectivity of tri-compound (mol %) | Conversion rate of metallic Si (wt %) |
|---|---|---|---|---|---|---|---|---|---|
| | Kinds | Amounts | | Tri-compound*1 | Tetra-compound*2 | Unreacted alcohol | Others*3 | | |
| Example 3 | aluminum powder | 1.0 g | 23 | 55.2 | 14.0 | 28.7 | 1.1 | 83 | 99.8 |
| Example 4 | aluminum silicon (Si content 10 wt %) | 1.0 g | 31 | 43.2 | 14.7 | 41.2 | 1.0 | 79 | 99.7 |
| Example 5 | aluminum silicon (Si content 10 wt %) | 0.5 g | 23 | 42.5 | 21.2 | 35.1 | 1.2 | 72 | 96.5 |

*1Tri-compound: triethoxysilane
*2Tetra-compound: tetraethoxysilane
*3Mainly diethoxysilane Analytical results of the composition of the whole liquid product, as well as the corresponding selectivity of triethoxysilane and conversion rate of silicon, are shown in Table 3.

EXAMPLE 9

The reaction was repeated in the same manner as in Example 7, except that 1 g of aluminum silicon (containing 10% by weight of silicon) was additionally fed to the reactor. The reaction finished after 30 hours.

Analytical results of the composition of the whole liquid product, as well as the corresponding selectivity of triethoxysilane and conversion rate of silicon, are shown in Table 3.

EXAMPLE 10

The reaction was repeated in the same manner as in Example 7, except that metallic silicon (containing 99.3% by weight of silicon, 0.25% by weight of aluminum and 0.22% by weight of iron, with a granular diameter on average of 100 μm) was used. The reaction finished after 25 hours.

Analytical results of the composition of the whole liquid product, as well as the corresponding selectivity of triethoxysilane and conversion rate of silicon, are shown in Table 3.

EXAMPLE 11

The reaction was repeated in the same manner as in Example 6, except that metallic silicon (containing 98.9% by weight of silicon, 0.38% by weight of aluminum and 0.43% by weight of iron, with a granular diameter on average of 100 μm) was used. The reaction finished after 18 hours.

Analytical results of the composition of the whole liquid product, as well as the corresponding selectivity of triethoxysilane and conversion rate of silicon, are shown in Table 3.

EXAMPLE 12

The reaction was repeated in the same manner as in Example 7, except that metallic silicon (containing 98.9% by weight of silicon, 0.41% by weight of aluminum and 0.50% by weight of iron, with a granular diameter on average of 100 μm) was used. The reaction finished after 16 hours.

Analytical results of the composition of the whole liquid product, as well as the corresponding selectivity of triethoxysilane and conversion rate of silicon, are shown in Table 3.

presence of a catalyst, in which the operation of using metallic silicon containing 0.30 to 0.37% by weight of aluminum, using cuprous chloride prepared by a wet process as catalyst, or allowing aluminum and/or an aluminum compound to coexist, are employed. The present process secures a high conversion rate of metallic silicon, and accordingly decreases the amount of unreacted metallic silicon, and suppresses discharge of industrial wastes with eliminating environmental problems.

We claim:

1. A process for producing trialkoxysilanes by reaction of a metallic silicon and an alcohol having 1 to 4 carbon atoms, in which the reaction is effected under at least one of the following conditions (1)–(3):
   (1) using as the metallic silicon one which contains 0.30 to 0.37% by weight of aluminum,
   (2) in the presence of a catalyst of cuprous chloride prepared by a wet process, and
   (3) allowing aluminum and/or an aluminum compound to coexist.

2. A process for producing trialkoxysilanes by reaction of a metallic silicon and an alkyl alcohol having 1 to 4 carbon atoms in the presence of a catalyst, in which the reaction is effected using as the metallic silicon one containing 0.30 to 0.37% by weight of aluminum and using cuprous chloride prepared by a wet process as the catalyst.

3. A process for producing trialkoxysilanes by reaction of a metallic silicon and an alkyl alcohol in the presence of a catalyst, in which the reaction is effected using as the metallic silicon one containing 0.30 to 0.37% by weight of aluminum, and allowing aluminum and/or an aluminum compound to coexist.

4. A process for producing trialkoxysilanes by reaction of a metallic silicon and an alkyl alcohol having 1 to 4 carbon atoms, in the presence of a catalyst, in which the reaction is effected using as the metallic silicon one containing 0.30 to 0.37% by weight of aluminum, and allowing aluminum and/or an aluminum compound to coexist, said catalyst being cuprous chloride prepared by a wet process.

5. A process according to any one of claims 1–4, in which the metallic silicon is one containing 0.31 to 0.36% by weight of aluminum.

6. A process according to any one of claims 1–4, in which the metallic silicon is one containing 0.32 to 0.35% by weight of aluminum.

7. A process according to any one of claims 1–4, in which the alkyl alcohol is methanol or ethanol.

TABLE 3

| | Reaction system | | | Composition of product (wt %) | | | | Selectivity of tri-compound (mol %) | Conversion rate of metallic Si (wt %) |
|---|---|---|---|---|---|---|---|---|---|
| | Aluminum content of metallic Si (wt %) | Time until finish of the reaction (hr) | Silicon content of aluminum silicon used (wt %) | Tri-compound*1 | Tetra-compound*2 | Unreacted alcohol | Others*3 | | |
| Example 6 | 0.32 | 26 | — | 49.5 | 5.7 | 44.0 | 0.8 | 91.6 | 96.7 |
| Example 7 | 0.31 | 30 | — | 44.0 | 12.2 | 44.0 | 0.9 | 83.3 | 89.1 |
| Example 8 | 0.36 | 27 | — | 44.4 | 9.0 | 43.4 | 1.0 | 86.2 | 90.0 |
| Example 9 | 0.31 | 30 | 10 | 43.6 | 9.2 | 46.5 | 0.7 | 85.7 | 99.7 |
| Example 10 | 0.25 | 25 | — | 44.9 | 14.6 | 39.4 | 1.1 | 91.8 | 79.6 |
| Example 11 | 0.38 | 18 | — | 59.3 | 10.2 | 29.3 | 1.2 | 88.0 | 76.4 |
| Example 12 | 0.41 | 16 | — | 55.0 | 7.2 | 35.8 | 1.4 | 90.7 | 62.8 |

*1Tri-compound: triethoxysilane
*2Tetra-compound: tetraethoxysilane
*3Mainly diethoxysilane Thus, the present invention is to provide a process for producing trialkoxysilanes by the reaction of a metallic silicon and an alcohol having 1 to 4 carbon atoms in the 8. A process according to any one of claims 1–4, in which the catalyst is used in an amount of 0.5 to 50 parts by weight based on 100 parts of said metallic silicon.

9. A process according to any one of claims 1–4, in which the catalyst is used in an amount of 5 to 30 parts by weight based on 100 parts of said metallic silicon.

10. A process according to claim 1, 3 or 4, in which said aluminum or said aluminum compound allowed to co-exist is an aluminum metal or an aluminum alloy.

11. A process according to claim 1, 3 or 4, in which said aluminum or said aluminum compound allowed to co-exist is in an amount of 0.01 to 10 parts by weight based on 100 parts of said metallic silicon.

12. A process according to claim 1, 3 or 4, in which said aluminum or said aluminum compound allowed to co-exist is in an amount of 0.1 to 2 parts by weight based on 100 parts of said metallic silicon.

* * * * *